United States Patent [19]

Kong-Chan

[11] Patent Number: 4,478,754
[45] Date of Patent: Oct. 23, 1984

[54] PREPARATION OF PHENYL ESTERS IN THE PRESENCE OF BORIC ANHYDRIDE

[75] Inventor: Josephine L. Y. Kong-Chan, West Chester, Ohio

[73] Assignee: The Procter & Gamble Company, Cincinnati, Ohio

[21] Appl. No.: 437,918

[22] Filed: Nov. 1, 1982

[51] Int. Cl.³ .................. C09F 5/08; C07C 69/00
[52] U.S. Cl. .................. 260/410.5; 560/130; 560/141; 560/142; 560/144
[58] Field of Search .................. 260/410.5; 560/130, 560/141, 142, 144

[56] References Cited

U.S. PATENT DOCUMENTS

| | | | |
|---|---|---|---|
| 2,822,378 | 2/1958 | Bader | 260/410.5 X |
| 2,833,825 | 5/1958 | Lewis | 260/410.5 X |
| 3,052,715 | 9/1962 | Rocklin | 260/410.5 X |
| 3,184,425 | 5/1965 | Jaruzelski et al. | 560/130 X |
| 3,557,167 | 1/1971 | Hülsmann et al. | 260/410.5 |
| 3,600,431 | 8/1971 | Taylor et al. | 260/410.5 X |
| 3,624,138 | 11/1971 | Murayama et al. | 560/130 |

*Primary Examiner*—Helen M. S. Sneed
*Attorney, Agent, or Firm*—Richard C. Witte; Ronald L. Hemingway

[57] ABSTRACT

An improved process for preparing carboxylic esters of phenols, in which the carboxylic acid and phenol are reacted in the presence of boric anhydride.

6 Claims, No Drawings

PREPARATION OF PHENYL ESTERS IN THE PRESENCE OF BORIC ANHYDRIDE

TECHNICAL FIELD

The present invention relates to a simple one-step reaction for the preparation of esters of phenols (i.e., phenyl esters), wherein a phenolic compound is reacted with a carboxylic acid in the presence of boric anhydride.

Carboxylic acid esters of phenol are known to be useful in such diverse fields as perfumery, medicine and light absorption in plastics. They are also useful as intermediates in the production of other useful compounds. For example, sulfonated carboxylic acid esters of phenol are useful as activators to increase the bleaching effectiveness of peroxygen bleaches such as sodium perborate (See Brit. Pat. No. 864,798, published Apr. 6, 1981).

BACKGROUND ART

U.S. Pat. No. 3,772,389, Lowrance, issued Nov. 13, 1973, discloses the reaction of phenols and carboxylic acids in the presence of a catalyst system consisting of a boron compound and sulfuric acid, to form the corresponding phenyl ester. Various boron compounds are disclosed, including boric anhydride. U.S. Pat. No. 4,271,311, Knickmeyer et al., issued June 2, 1981, discloses the reaction of phenols with carboxylic acids in the presence of a catalyst system consisting of a boron compound and certain alkali metal salts. Boric anhydride is among the boron compounds disclosed. The Lowrance and Knickmeyer patents are incorporated by reference herein.

SUMMARY OF THE INVENTION

The present invention is an improved process for preparing a phenyl ester by reacting a phenol with a $C_2$ to $C_{20}$ carboxylic acid, wherein the reaction is conducted in the presence of boric anhydride at a molar ratio of boric anhydride to carboxylic acid of from about 0.4:1 to about 1.6:1, the said reaction being conducted in the substantial absence of sulfuric acid, alkali metal borates, alkali metal polyborates, alkali metal hydroxides and alkali metal borohydrides.

DESCRIPTION OF THE INVENTION

In accordance with the present invention it has been found when the reaction of a phenol and a carboxylic acid is conducted in the presence of an amount of boric anhydride which is in a molar ratio of from about 0.4:1 to about 1.6:1 to the carboxylic acid, the sulfuric acid and the alkali metal salts disclosed as co-catalysts in the Lowrance and Knickmeyer patents, supra, are unnecessary. In fact, in some instances the presence of these co-catalysts can be detrimental to the overall yield of the reaction and/or purity and color of the phenyl ester product.

Accordingly, the present invention is an improved process for preparing a phenyl ester of a carboxylic acid by reacting a phenol with a $C_2$ to about $C_{20}$ carboxylic acid, the improvement comprising the step of conducting the reaction in the presence of boric anhydride, in a molar ratio of approximately 0.4:1 to about 1.6:1 of boric anhydride to the carboxylic acid, said reaction being conducted in the substantial absence of sulfuric acid, alkali metal borates, alkali metal polyborates, alkali metal hydroxides and alkali metal borohydrides.

By "substantial absence" of the above recited co-catalysts, it is meant that none of said materials is present in the reaction mix at a level which has any detectable effect on the reaction or the reaction product.

Examples of carboxylic acids used in the process of the invention are those which have the formula RCOOH wherein R is a hydrocarbyl radical containing from 1 to about 19 carbon atoms. The hydrocarbyl group can be saturated or unsaturated straight or branched chain, aliphatic or aromatic, and can be substituted with radicals such as halogen, nitro groups and alkoxy groups. Aliphatic R groups include methyl, propyl, 3-chloropropyl, pentyl, 4-nitropentyl, dodecyl, octadecyl, octadecenyl, isopropyl, and isodecyl. Aromatic groups include phenyl, naphthyl, toluyl, 4-chlorophenyl, 4-nitrophenyl and 3-ethoxyphenyl. Preferred carboxylic acids are the saturated aliphatic carboxylic acids such as acetic, propionic, butyric, valeric, caproic, caprylic, capric, lauric, myristic, palmitic, and stearic. Examples of unsaturated acids which can be used include oleic, palmitoleic and linoleic.

Phenol compounds used as reactants in the process herein are those which have the formula

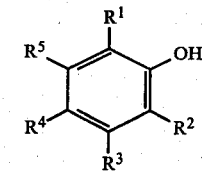

At least one of the carbon atoms adjacent the carbon atom bearing the OH group is unsubstituted, i.e., at least one of the substituents $R^1$ and $R^2$ of the formula must be a hydrogen atom while the remaining adjacent substituent, as well as the substituents $R^3$-$R^5$, can be the same or different monovalent substituents bound to the ring by a covalent bond and can be any such substituent which does not sterically hinder or otherwise prevent the hydroxyl group of the phenolic compound from entering into the reaction with the carboxylic acid compound.

Typical monovalent substituents which are suitable include halogen atoms and alkyl, aryl, substituted aryl, hydroxy, alkoxy, aryloxy, amino, substituted amino, quaternized ammonium, substituted sulfonyl, fluorinated alkyl, cyano, thiocyano, thiol and nitro groups, for example. The monovalent substituents named are illustrative, and not limiting, because, as noted, any monovalent substituent bound to the ring by a covalent bond which does not sterically hinder or destroy the ability of the hydroxyl group of the phenolic compound to enter into the reaction with the carboxylic compound can be present. Any or all of the substituents $R^1$-$R^5$ may also be hydrogen atoms, and as previously noted, at least one of the substituents $R^1$ or $R^2$ must be hydrogen.

Chlorine, bromine, fluorine and iodine atoms are illustrative of the halogen atoms which are suitable as substituents. When one or more of the substituents is alkyl, it can have 1 to 18 carbon atoms, and preferably 1 to 12, such as methyl, ethyl, propyl, isopropyl, n-butyl, isobutyl, tertiary butyl, n-pentyl, tertiary amyl, n-hexyl, n-decyl, n-dodecyl, n-hexadecyl, n-octadecyl or tertiary octyl, for example.

Suitable aryl or substituted aryl substituents are preferably mononuclear aryl of from 6 to 12 carbon atoms such as phenyl, methylphenyl, ethylphenyl, chlorophenyl, bromophenyl, methoxyphenyl, ethoxyphenyl or other substituted phenyl nuclei. However, an aryl nucleus of 4 or more carbon atoms such as 1-naphthyl or 2-naphthyl and substituted derivatives thereof such as, for example, furyl, thienyl, etc., can be formed involving adjacent R groups and are included in the term "aryl" as used herein.

Illustrative of the alkoxy groups suitable as substituents are alkoxy groups having from 1 to 18 carbon atoms and preferably from 1 to 6 carbon atoms, such as methoxy, ethoxy, propoxy, isopropoxy, n-butoxy, isobutoxy, n-amyloxy, isoamyloxy and hexoxy, for example.

Phenoxy and naphthoxy are illustrative aryloxy groups which may be used as substituents and may have from 6 to 12 carbon atoms.

Monoalkylamino, dialkylamino (wherein the alkyl groups are the same or different), arylamino, aralkylamino, cycloalkylamino, monohydroxyalkylamino, dihydroxyalkylamino, alkoxyalkylamino and other aliphatic amino groups, for example, are illustrative of the substituted amino groups which may be substituents. Normally the alkyl, hydroxyalkyl or alkoxyalkyl groups present in such amino groups contain no more than 4 carbon atoms although they can contain more.

Illustrative of the substituted sulfonyl groups which may be present in the $R^1$ or $R^2$ and/or $R^3-R^5$ positions are alkyl-sulfonyl groups having from 1 to 18 carbon atoms and preferably from 1 to 4 carbon atoms such as methylsulfonyl, ethylsulfonyl, propylsulfonyl, butylsulfonyl, etc., and arylsulfonyl, preferably mononuclear arylsulfonyl such as phenylsulfonyl, methylphenylsulfonyl, chlorophenylsulfonyl and ethoxyphenylsulfonyl.

R or $R^2$ and/or $R^3-R^5$ can also be a fluorinated alkyl group having 1 to 18 carbon atoms. Difluoroalkyl groups having the formula $-(CH_2)_xCHF_2$ and trifluoroalkyl groups having the formula $-(CH_2)_xCF_3$ wherein X is a positive integer of from 1 to 17 are illustrative. Higher fluorinated alkyl groups such as

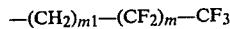

$-(CH_2)_{m1}-(CF_2)_m-CF_3$ wherein m is a positive integer from 1 to 4, for example, and m1 is a positive integer of 1 or 2, can also be present and are intended to be included in the term "fluorinated alkyl" with 2,2-difluoroethyl; 3,3-difluoro-n-propyl; 4,4-difluoro-n-butyl; 5,5-difluoro-n-amyl; 6,6-difluoro-n-hexyl; 2,2,2-trifluoroethyl; 3,3,3-trifluoro-n-propyl; 4,4,4-trifluoro-n-butyl; 5,5,5-trifluoro-n-amyl; 6,6,6-trifluoro-n-hexyl; $-CH_2CH_2CF_3$; $-CH_2CH_2CF_2CF_3$; $-CH_2CH_2CH_2CF_2CF_3$ and $-CH_2CH_2CF_2CF_2CF_3$ being illustrative of such fluorinated alkyl groups.

$R^1$ or $R^2$ and/or $R^3-R^5$ are not limited to the particular substituents noted herein. As stated hereinbefore, $R^1-R^5$ can be any monovalent substituent, bound by a covalent bond, so long as the hydroxyl group of the phenolic compound is not prevented by the substituent from entering into the reaction with the carboxylic compound.

Boric anhydride has the formula $B_2O_3$ and is commercially produced by heating boric acid to fusion temperature.

In the conduct of the reaction, the molar ratio of carboxylic acid to phenolic compound is desirably between about 1:1 and about 0.25:1, preferably from about 0.75:1 to about 0.5:1. The molar ratio of boric anhydride to carboxylic acid should be from about 0.4:1 to about 1.6:1, preferably from about 0.8:1 to about 1.2:1.

The reaction is typically carried out at atmospheric pressure and a temperature between about 185° C. and 250° C., preferably from about 185° C. to about 200° C. Reaction time will vary, depending on the temperature used. Typically a reaction time of about 5 hours will be sufficient at a temperature of about 185° C. The progress of the reaction can be followed by periodic determination of the unesterified carboxylic acid content of the reaction mix. If higher temperatures are desired, superatmospheric pressure can be used.

If the reaction is conducted above the melting point of the reactants, no solvent is necessary. If it is desired to use a solvent, high boiling solvents such as diphenyl ether or 2ethylhexyl ether, can be used.

Water is formed as a product of the reaction and this should be removed from the reaction system as the reaction proceeds. If the reaction temperature is sufficiently high, the water or an azeotrope of water and solvent can be removed by distillation, use of a Dean-Stark trap, etc. Likewise, water-absorbing granular materials such as molecular sieves, silica gels, etc., can be incorporated into the reaction mix to take up the water of reaction.

At the end of the reaction the hot reaction mix can be filtered to remove any solids (e.g., granular water absorbents and/or boric acid formed during the reaction). The liquid reaction mix can then be vacuum distilled to isolate the phenyl ester.

The invention will be illustrated by the following example.

EXAMPLE 100 gm (0.649 mole) of a mixture of saturated $C_8$ to $C_{10}$ fatty acid, 122.4 gm (1.30 moles) phenol, and 25 g of 4 A° molecular sieve were charged to a 500 ml, 4-necked, round bottom flask, fitted with a mechanical stirrer, nitrogen gas purge, thermometer and condenser. The reaction mix was stirred under nitrogen at 120° C. for 1 hour. 45.20 gm (0.649 mole) of boric anhydride (Fisher Scientific) was then added and the reaction temperature was raised to 185° C. under nitrogen.

Progress of reaction was determined by gas chromatography. By the end of 5 hours, it was determined that at least 80% of the fatty acids had been converted to their corresponding phenyl esters. No other side products were detected by gas chromatography. The color of the reaction mix was pale brownish yellow.

The reaction was terminated by cooling the reaction mix down to about 100° C. The reaction mix was then filtered hot. The desired phenyl ester was then obtained by vacuum distillation of the filtrate at 105° C. to 160° C. at 1 mm Hg. The yield was 131.89 gm (0.573 moles, 88.3% of theoretical) of the $C_8$ to $C_{10}$ carboxylic esters of phenol.

What is claimed is:

1. An improved process for preparing a phenyl ester of a carboxylic acid by reaction of a phenol compound with a $C_2$ to $C_{20}$ carboxylic acid wherein at least one of the carbon atoms adjacent the carbon atom bearing the OH group in the phenol compound is unsubstituted, the improvement comprising the step of conducting the reaction in the presence of boric anhydride in a molar ratio of boric anhydride to carboxylic acid of from about 0.4:1 to about 1.6:1, said reaction being conducted in the substantial absence of sulfuric acid, alkali metal borates, alkali metal polyborates, alkali metal hydroxides and alkali metal borohydrides.

2. The process of claim 1 wherein the carboxylic acid has the formula RCOOH, wherein R is a saturated aliphatic group containing from 1 to about 19 carbon atoms and the phenol compound has the formula

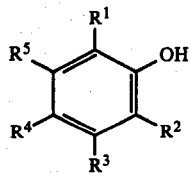

wherein at least one of the substituents $R^1$ or $R^2$ must be hydrogen while the remaining substituent, as well as the substituents $R^3$–$R^5$, can be the same or different and are selected from the group consisting of hydrogen, halogen, $C_1$ to $C_{18}$ alkyl, $C_6$ to $C_{12}$ aryl, hydroxy, $C_1$ to $C_{18}$ alkoxy, $C_1$ to $C_{12}$ alkyl- or aryl-substituted amino, $C_1$ to $C_{18}$ alkylsulfonyl or arylsulfonyl, $C_1$ to $C_{18}$ fluorinated alkyl, cyano, thiocyano, thiol and nitro.

3. The process of claim 2 wherein the molar ratio of boric anhydride to carboxylic acid is from about 0.8:1 to about 1.2:1.

4. The process of claim 3 wherein the phenol compound is phenol.

5. The process of claim 4 wherein the carboxylic acid is a $C_8$ to $C_{10}$ fatty acid.

6. The process of claim 5 wherein the molar ratio of boric anhydride to carboxylic acid is 1:1.

* * * * *